The United States Patent [19]

Kozikowski et al.

[11] Patent Number: 4,792,341
[45] Date of Patent: Dec. 20, 1988

[54] HAIR PHOTOBLEACHING

[75] Inventors: Stan D. Kozikowski, Stamford; J. Menkart, Greenwich; L. J. Wolfram, Stamford, all of Conn.

[73] Assignee: Clairol Incorporated, New York, N.Y.

[21] Appl. No.: 876,319

[22] Filed: Jun. 19, 1986

[51] Int. Cl.$^4$ ............................................. D06L 3/04
[52] U.S. Cl. ..................... 8/103; 8/127.51; 8/115.52; 204/157.61; 204/901
[58] Field of Search ............... 8/103, 115.52; 204/133, 204/134, 135, DIG. 11, 157.3, 157.61, 157.15, 901; 424/70

[56] References Cited

U.S. PATENT DOCUMENTS 3,281,263 10/1966 Priesing et al. ..................... 8/128 A
3,941,670 3/1976 Pratt, Jr. ......................... 204/157.61

OTHER PUBLICATIONS

N. M. Bikales, (Exec. ed.) Encyclopedia of Polymer Science and Technology, vol. 11, p. 702 (1969).
J. Soc. Cosmet. Chem., 82, 179–191 (May/Jun. 1987) "Chemical– and Photobleaching of Brown and Red Hair" by L. Wolfram and L. Albrecht.

Primary Examiner—Paul Lieberman
Assistant Examiner—John F. McNally
Attorney, Agent, or Firm—Sandra M. Person

[57] ABSTRACT

A method and apparatus for artificially bleaching or lightening hair by exposing the hair to intense radiation of artificial light. The light is typically from a laser or flashlamp source and provides adequate intensity and power during the lifetime of the excited melanin molecule in the hair to substantially destroy at least some of the melanin molecules in the hair.

10 Claims, 3 Drawing Sheets

HAIR PHOTOBLEACHING

BACKGROUND OF THE INVENTION

This invention relates to a bleaching of hair, and more particularly to the use of intense radiation of artificial light for the bleaching of hair.

It is known that the coloring of hair is dependent upon the melanin content of the hair and such coloration is directly proportional to the melanin content. To some degree melanin has been shown to act as a "black hole" (D. Slawinska and J. Slawinski, Electronically Excited Molecules in the Formation and Degradation of Melanins, Physiol. Chem. Phys., 14, 363–374, 1982). The intensity of the photon field inside melanin might be higher than the external one by many orders of magnitude. The energy of the excited state of melanin stemming from light absorption is then dissipated as heat in the process based upon a single common mechanism, the electron-photon interaction (J. McGinnes and P. Proctor, The Importance of the Fact that Melanin is Black, J. Theor. Biol., 39 677–678, 1973).

Bleaching of hair color is typically performed through chemical means utilizing ammoniacal solutions of $H_2O_2$ to degrade the melanin pigment. Although chemical bleaching of hair is very effective, it suffers from the disadvantage of causing significant oxidative hair damage as well as requiring lengthy treatment time to obtain sufficient color changes.

It is a common observation that prolonged exposure of hair to sunlight results in hair bleaching. The extent of such color change is a function of the initial hair coloring and the lightening process is very slow. Even during summertime, it takes many days of exposure in order to obtain perceptible hair lightening.

While our understanding of this bleaching process is not complete there is substantial experimental evidence suggesting that the lightening effect results from an interplay of physical (light absorption) and chemical ($H_2O_2$ generation) factors.

Clearly, a possibility of relying exculsively on the light energy to bleach the hair (pure photobleaching) cannot be discounted and, indeed, this aspect has been brought up in a recent publication ("Laser And Hair", Tech. News, *Laser Focus*, Vol. 19, No. 9, p. 26, September 1983). However no practical efforts in this direction have been reported and no appreciation of, nor an understanding of the requirements of hairphotobleaching has been achieved.

SUMMARY OF THE INVENTION

Although the melanin can absorb very high energy and power levels and convert this energy to heat, it appears that above some energy, and/or power level of excitation, the capacity of melanin to convert all of the absorbed light energy into heat does not exist any longer. This results in sudden damage to its structure and consequently partial chemical disintegration. This process leads to the radiative bleaching of melanin.

Through various tests, it has been found that high intensity light sources, such as laser or high pressure arc flash lamps, can produce adequate energy/power levels of excitation to produce such hair lightening.

Depending upon the type of radiative source being utilized, the wavelength, intensity and power can be varied. However, adequate radiation is required to destroy or disintegrate the melanin. Lightening or color change results from either the melanin disintegration itself or as a result of non-selective scattering of light on the cavities randomly left by the melanin granules which have disintegrated.

Various experiments were conducted. By way of example, using a neodymium laser producing a wavelength of 530 nm (second harmonic of the $Nd^{3+}$:glass laser) photobleaching occurred with light energy intensity of approximately 45 $\mu J/mm^2$ to 150 $\mu J/mm^2$ delivered to the hair sample during 1.5 nsec which constitutes the lifetime of the melanin excited state (singlet). Other values were produced by different lasers. Also, flashlamps with adequate energy and power densities may be able to produce similar results.

Accordingly, it is an object of the present invention to provide a method of bleaching hair by exposing the hair to a burst or bursts of intense radiation of artificial light.

A further object of the present invention is to provide hair photobleaching by application of artificial light radiation sufficient to decompose the melanin in the hair.

Another object of the present invention is to provide a photobleaching of the hair through application of multiple pulses of intense radiation from artificial light.

Still a further object of the present invention is to provide a method of hair bleaching by the use of laser light.

Another object of the present invention is to provide photobleaching of the hair through application of light emitted from a flashlamp.

Still another object of the present invention is to provide lightening of the hair through non-selective light scattering resulting from the production of scattering centers or cavities induced within the hair structure.

These and other objects, features and advantages of the invention will, in part, be pointed out with particularity and will, in part, become obvious from the following more detailed description of the invention, taken in conjunction with the accompanying drawings, which form an integral part thereof.

DESCRIPTION OF THE PREFERRED EMBODIMENT

Hair color is directly associated with the presence in the fiber of the melanin pigment. Melanin granules have an internal photon field which is higher than the external one by many orders of magnitude. The energy of the excited state of melanin resulting from light absorption is dissipated as heat during the process based upon the electron photon interaction. The melanin pigment shows extremely high resistance against very intense streams of radiative energy, thereby making melanin capable of playing its protective role as a sun screen for biologically harmful radiation. Very high energy/power levels of light originating from sources such as lasers interacting with the melanin normally can be absorbed and common transfer of this energy into heat takes place.

Above some energy and/or power level excitation, the capacity of melanin to convert all of the absorbed light energy into heat does not exist any longer. This results in sudden damage to its bonds and partial chemical disintegration, the process leading to the radiative bleaching of melanin. The possibility of photobleaching is therefore dependent upon the energy/power requirements.

To evaluate specific requirements for light-induced breakage of chemical bonds, one should start with the simple Planck formula for the energy (E) of a single quantum $$E = h\nu = \frac{hc}{\lambda}$$

where h is the universal Plank constant, $h = 6.62 \times 10^{-34}$ joule $\times$ sec.

c is the velocity of light in vacuum, $c = 3.0 \times 10^8$ m$\times$sec$^{-1}$.

$\nu$, $\lambda$ are the frequency and the wavelength of the light used, respectively.

For any chemical compound featuring a bonding energy of E, in terms of kilocalories of energy provided for one mole of this compound ($\xi$), there is a relation $$\xi = h c A/\lambda$$

where A is the Avogadro number, $A = 6.02 \times 10^{23}$.

The wavelength of radiation capable of breaking bonds for any value of energy ($\xi$) is then $$\lambda = h c A/\xi$$

In order to get $\lambda$ in nanometers (with $\xi$ in kilocalories), one should properly convert all the units of the above relation which results in $$\lambda = 28,562.2/\xi \text{(nm)}$$

This last relationship allows one to calculate $\lambda$ vs. breakage energy $\xi$, expressed in kilocalories. Results calculated using this expression are shown graphically in FIG. 1.

Figure 1:
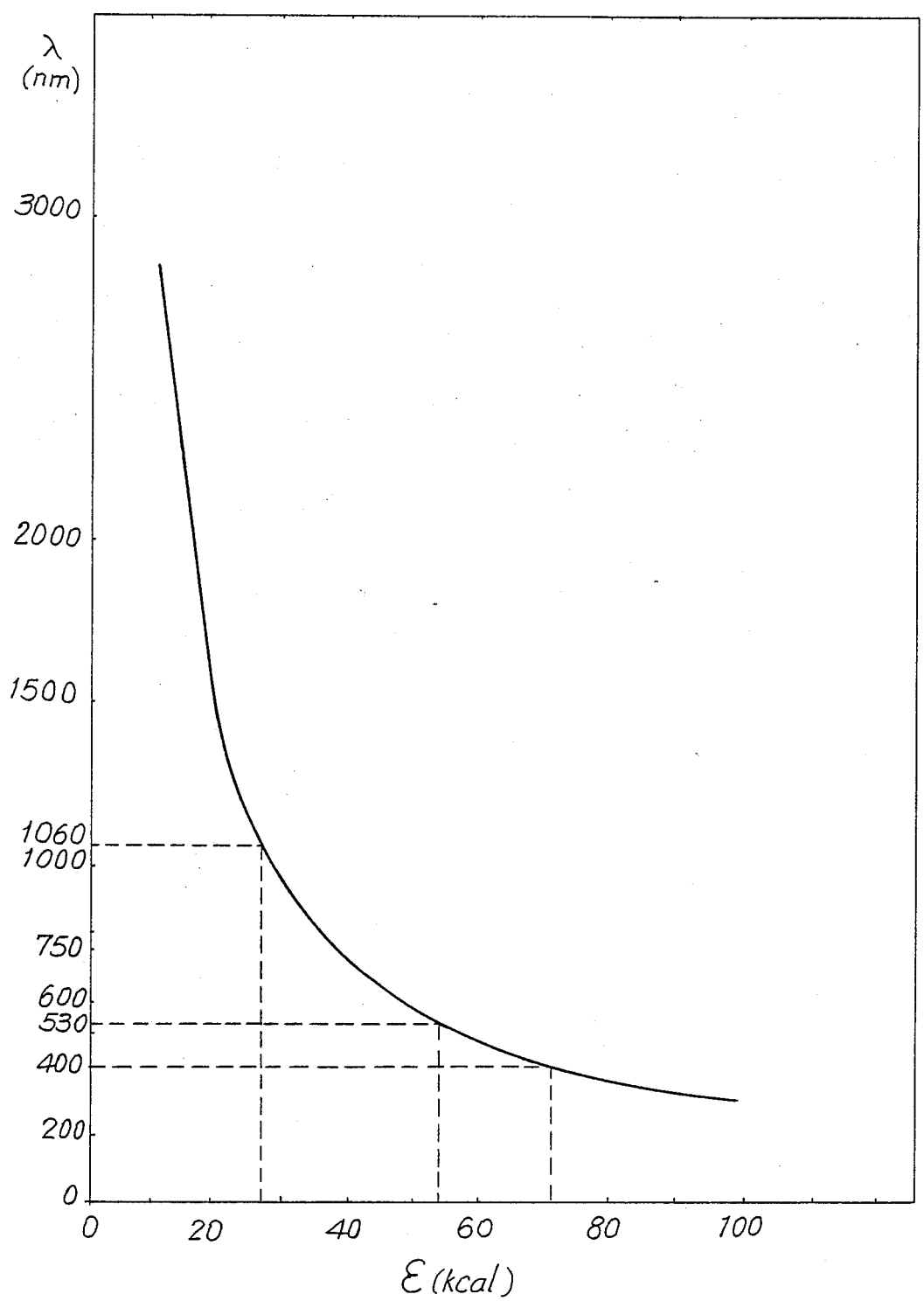
FIG. 1 is a graph showing light wavelength vs. energy of a light source usable in the theoretical explanation of the destruction of the melanin molecule.

As can be seen in FIG. 1, wavelengths of the visible spectrum ranging from 400 nm up to 750 nm correspond to the energy range of 71 kcal to 38 kcal, respectively. Thus, any wavelength from the red end of the visible spectrum provides sufficient amount of energy to break bonds of chemical compounds if their binding energy amounts to less than about 40 kilocalories per 1 mole. The next requirement is that of sufficient density of light energy to make the expected effect significant. The latter condition seems to be well met by any laser yield of proper wavelength and of sufficient intensity. The ruby laser with its wavelength of 694.3 nm and with its relatively high pulse energy output provides a very good means to accomplish light breakage of chemical bonds of 41.3 kcal per mole. The second harmonic of the neodymium YAG or glass laser of $\lambda = 530$ nm wavelength is even better, allowing breakage of bonds up to 53.9 kcal per mole. The basic yield of neodymium laser, however, would not seem to be a suitable source for the experiment because its wavelength of $\lambda = 1.06$ $\mu$m corresponds to an energy of only 26.9 kcal per mole. This amount is evidently much below the threshold energy of about 40 kcal corresponding to the melanin bonds. However, it appears that two-photon transitions are involved in the process of the laser-radiation hair bleaching and, accordingly, the useful spectral range can be extended toward longer wavelengths of 1.06 $\mu$m and probably more. The only restriction in proceeding farther into the IR spectrum appears to be an increasing absorption of keratin which is the main hair component.

Various experiments were conducted utilizing different types of lasers and flashlamps. The test showed that the light energy density requirements for optimal photobleaching were at about 45 $\mu$J/mm$^2$ to 150 $\mu$J/mm$^2$ at 530 nm wavelength (2nd harmonics of the Nd$^{3+}$:glass laser), delivered to the hair sample during the 1.5 nsec lifetime of the melanin excited state (singlet). The corresponding value for 1.06 $\mu$m wavelength (the basic output of the Nd$^{3+}$:glass laser) was about 150 $\mu$J/mm$^2$. Good results were also obtained using a flashlamp pumped dye laser emitting $\lambda = 590$ nm wavelength, as well as by the use of an excimer laser filled with N$_2$ and providing a $\lambda = 337$ nm wavelength. Generally, better results were obtained with multiple pulses (5 to 10 and more) in a sequence. Other lasers and flashlamps attaining the threshold energy/power requirements may allow them to produce similar results of hair photobleaching.

Figure 2:
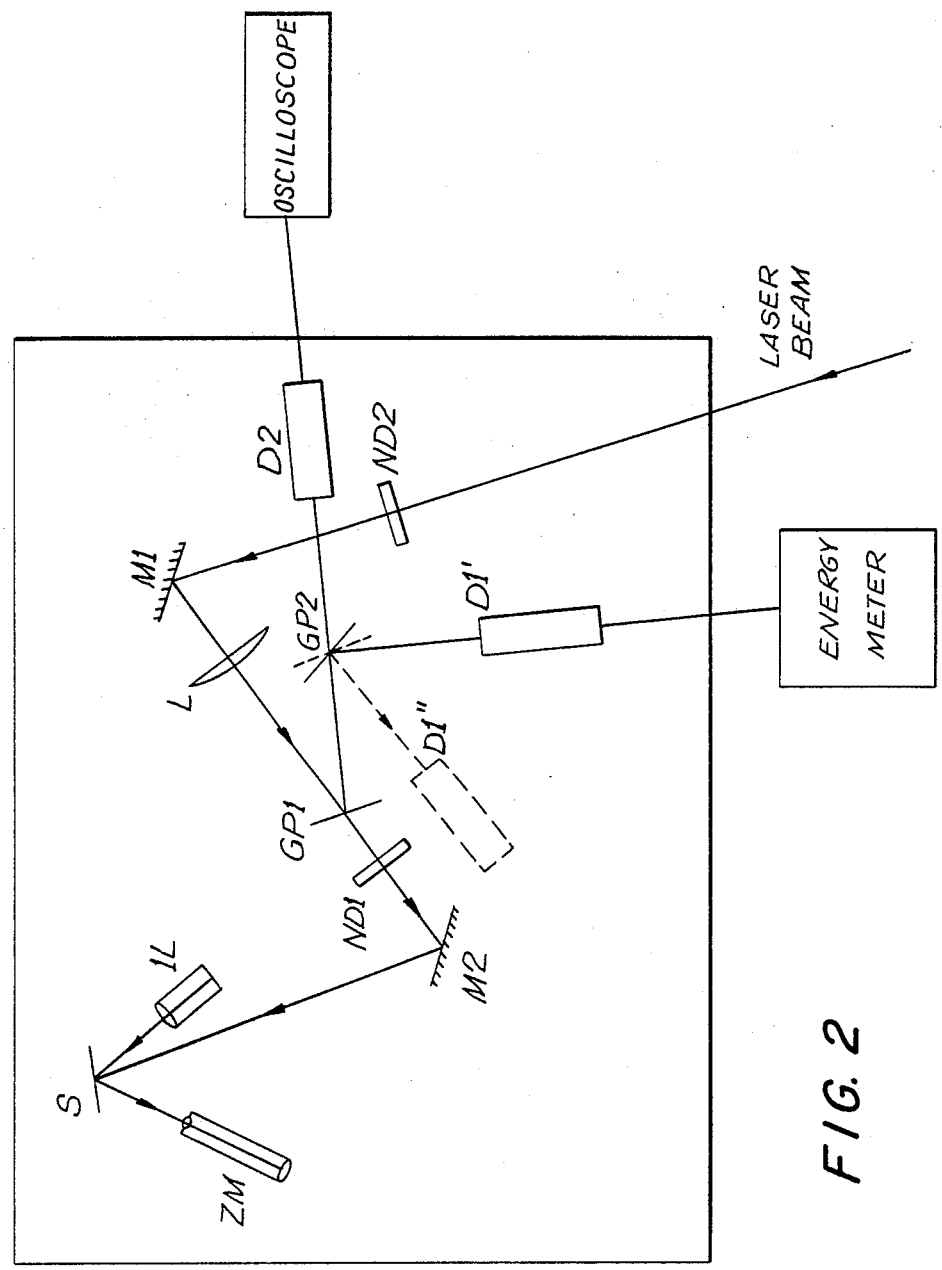
FIG. 2 is a schematic diagram of an apparatus used for testing the bleaching of hair using a laser source.

The experimental set-up used to demonstrate the above results are shown in FIG. 2. A beam from a neodymium laser (model DCR Nd:YAG Laser made by Quanta Ray) enters the system from the bottom right. After reflecting on the first mirror (M1), it passes through the lens (L) of one meter focal length which is approximately the distance from the lens (L) to the sample. The beam is then directed by the mirror M2 to reach the sample (S). Two glass plates (GP) were employed to provide the proper fraction of the laser-beam energy to be concurrently measured during the experiments, one (GP1)—to extract a small part of laser energy from the main beam, and the second (GP2)—to divide this extracted part into two much weaker parts suitable to safely interact with photodetectors (D1 and D2). Photodetector D1 may be used in two locations dependent upon the wavelength employed: D1' configuration was mostly used with $\lambda = 530$ nm, and D1" with 1.06 $\mu$m. The dielectric selective mirrors (M1 and M2) may be replaced in order to be well matched to the wavelength applied. The D1 signal was sent directly to the energy meter (Model Rj-7100 made by Laser Precision Corp.) which provides the instant energy and number of pulses readouts, and the D2 signal is displayed on the CRT of a Tectronix 7904 Oscilloscope, thus giving the laser pulse duration. The energy of the laser beam interacting with the hair sample (S) could be regulated in three independent ways:

1. by regulating the laser supply level,
2. by inserting various neutral density (ND) filters into the laser beam; for the lower level of the laser supply only the ND1 position was used and for the higher level of the laser supply, both the ND1 and ND2 were employed,
3. by shifting the sample along the beam, which results in a change of the beam cross section thus allowing regulation of the energy density affecting the sample.

In order to better adjust the sample, the stereo zoom microscope (ZM) was used (Bausch & Lomb) along with a regular microscope illuminating lamp (IL).

Hair samples were prepared as tresses made of many hair fibers glued at both sides to plastic plates of 1×1.5 inch size. The sample itself was composed of hundreds of fibers stretched between two plates thus making a densely packaged multiple layer of hair. The effective size of such a hair sample was about 1×2 inches. The sample was held and stretched by a holder which provided precise x-, y- and z- regulations, thus allowing exposure of subsequent areas of the sample to the laser radiation.

In our preliminary experiments carried out with a neodymium glass laser the sample (S) was placed slightly out of focus of the collimating lens (L), a location which defined the area of interaction of the sample with the laser-beam energy, as being of 0.1 to 0.7 mm$^2$.

In recent experiments the flashlamp-pumped dye-laser ($\lambda$=590 nm) was used which thanks to its high energy output (more than 1 joule in 0.5 $\mu$s pulse duration), allowed us to photobleach the hair sample areas as large as 0.5 cm$^2$.

Various hair samples made of brown intact hair were exposed to laser radiation following the procedure described above. Also, films containing squid melanin were used as samples. They were prepared as a mixture of a water solution of polyvinyl alcohol (PVA) with squid melanin. The mixture was poured out on a glass substrate and peeled off after evaporation. PVA is an ideal host material because of its very high transparency in the visible and infrared spectra area. Both the natural-state and after-solubilization squid melanin were used for sample preparation the first resulting in a much more inhomogenous distribution of melanin than the latter one. A pure PVA sample was also prepared as a reference.

In conducting the bleaching experiment the $\lambda$=530 nm green line (second harmonic of the neodymium laser yield) and the basic line of the laser ($\lambda$=1.06 $\mu$m) were used. Both the green and infrared laser-energy supplies were used with various output energy levels in the single pulse and in the multiple pulse regimes.

As can be seen from FIG. 2, the measured energy ($\xi$) differs from the energy which hits a sample (E), both convertible one into another through a conversion factor (F), $$E = F \times \xi$$

where $$F = \frac{92\%}{R1 \times R2} \times ND$$

and where R1 and R2 are the reflectances of the GP1 and GP2, respectively, ND is the transmittance of the ND1 neutral density filter employed, and 92% is the transmittance of a single glass plate.

It is a well known disadvantage of all pulse lasers that their beam cross-section features highly inhomogeneous energy distribution. One of the simplest and most effective methods of improving this condition is by inserting an optical scatterer into the laser beam just in front of the sample which is to be irradiated. This results in significant flattening of energy distribution across the laser beam but at the same time it introduces some attenuation of energy in use, which must be taken into account while processing the results. A regular glass scatterer was utilized in many of the experiments reported herein.

The experiments using the set up of FIG. 22 produced a great variety of results of laser beam interaction with natural hair samples and with film samples containing melanin. Numerous sample spots were tried for a wavelength of 530 nm and for 1.06 $\mu$m (neodymium glass laser: its second and first harmonics, respectively), and also for 590 nm (dye-laser). Both single pulse and multiple pulses were tried and both the use with and without a scatterer were tried. In each case, the sample was evaluated for the amount of laser impact ranging from no effect and proceeding along a scale from very weak bleaching towards well bleached results, and continuing to overbleached and finally toward hair which was damaged and ultimately broken and burnt.

Sample spots were also taken for both hair samples that were dry as well as hydrated hair samples. Synthetic samples were also used with three specific synthetic samples including the solublized squid melanin in PVA, insoluble squid melanin in PVA, and pure PVA as a reference.

A summary of the results obtained in terms of the energy/power density is presented in Table I which gives the optimal conditions for hair bleaching by laser radiation using two particular laser lines of 530 nm and 1.06 $\mu$m.

TABLE I

OPTIMAL CONDITIONS OF HAIR/MELANIN BLEACHING BY LASER LIGHT OF 530 nm. AND 1.06 $\mu$m

| | Single Pulse | | Multiple Pulse | | | |
| --- | --- | --- | --- | --- | --- | --- |
| | | | Individual Pulse | | Sequence Pulses (10) | |
| | Energy Density (m∂/mm$^2$) | Power Density (MW/mm$^2$) | Energy Density (m∂/mm$^2$) | Power Density (MW/mm$^2$) | Total Energy Density (m∂/mm$^2$) | Ave. Power Density (mW/mm$^2$) |
| Hair Sample $\lambda$ = 0.53 | | | | | | |
| w/o scatterer | <0.4 | <0.1 | 0.12–0.04 | 0.03–0.1 | 1.2–0.4 | 1.2–4.0 |
| w/scatterer | <<1.5 | <<0.15 | 1.2–2.2 | 0.3–0.5 | 12–22 | 12–22 |
| Hair sample $\lambda$ = 1.06 um w/scatterer | <<1.8 | 0.45 | ~0.4 | ~0.1 | ~4.0 | ~4.0 |
| Intact squid melanin PVA (1% p.w.), $\lambda$ = 0.53 um | | | | | | |
| w/scatterer | 1.24–1.37 | 0.03–0.34 | 0.24–8.28 | 0.06–0.2 | 2.4–8.4 | 2.4–8.5 |
| w/o scatterer | ~0.25 | 0.06 | | | | |
| Solubilized squid melanin | 3.8 (1.6–4.3) | 0.95 (0.4–1.1) | ~1.2 | ~0.3 | ~12 | ~12 |

TABLE I-continued
OPTIMAL CONDITIONS OF HAIR/MELANIN BLEACHING BY LASER LIGHT OF 530 nm. AND 1.06 μm

| | Single Pulse | | Multiple Pulse | | | |
| --- | --- | --- | --- | --- | --- | --- |
| | | | Individual Pulse | | Sequence Pulses (10) | |
| | Energy Density (mJ/mm$^2$) | Power Density (MW/mm$^2$) | Energy Density (mJ/mm$^2$) | Power Density (MW/mm$^2$) | Total Energy Density (mJ/mm$^2$) | Ave. Power Density (mW/mm$^2$) |
| in PVA (1% p.w.) $\lambda$ = 0.53 um w/scatterer | | | | | | |

As is seen from Table I, the regular optical scatterer utilized introduced effective attentuation of the laser beam of about ten-fold.

It was uncertain whether the white color of hair after the laser irradiation come mostly from melanin decomposition or just from the surface or volume mechanical destruction of hair, resulting in very effective light scattering. A simple test was performed to get the answer. Hair samples already bleached by laser light were swollen in formic acid, thus becoming very transparent. If the samples were just affected on their surface or in their volume but still contained melanin, the hydration which restores the optical homogeneity of thus revealing the presence of still intact melanin. the sample should bring it back to its original color, However, microscopic viewing of such a hair hydrated after being bleached indicates significant loss of the melanin pigment. This indicated that the bleaching that occurred has its source to a substantial extent in the decomposition of melanin by the laser irradiation.

Figure 3:
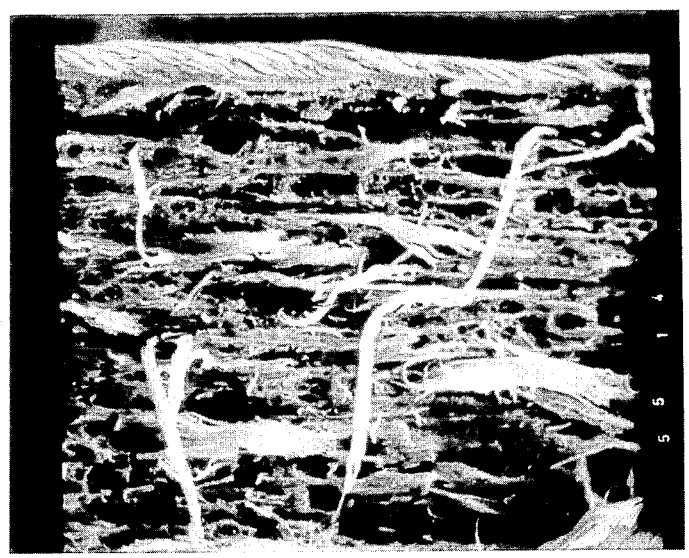
FIGS. 3A and 3B show electron microscopic pictures of laser bleached hair which is respectively torn along its length and cut along its length for analysis of the melanin destruction of the hair.
Figure 4:
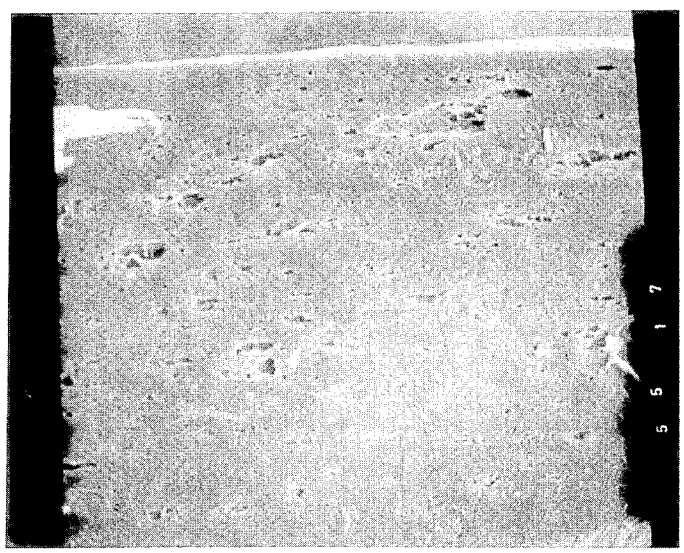

The hair fibers were examined in an electron ($\times$1000) microscope test and FIGS. 3 and 4 show electromicrophotographs of two well bleached hair samples. These figures reveal cavities forming elongated vacuoles the extent of which become more apparent with increasing level of radiation energy/power employed.

These cavities are clearly associated with the destruction of the pigment brought about by laser radiation. It is not certain at this stage whether the observed vacuoles represent only the burnt-out granules of melanin or, in more general terms are also the results of explosive breakdown of the pigment which also effects the surrounding hair matrix. Both types of cavities form a system of the light scattering centers which can significantly enhance the bleaching effect of melanin decay.

It therefore appears that the bleaching may be the result of two mechanisms. Firstly, the melanin disintegration results in an elimination of the melanin thereby bleaching the hair by removing the pigmentation. Additionally, there appears to be a non-selective scattering of light on small cavities randomly distributed within the hair volume.

The foregoing tests with the laser light show that with the neodymium glass laser as a source of the high intensity radiation good results were achieved. The second harmonic of 530 nm wavelength produced good results of 30 μJ to 100 μJ energy and of a 4 ns pulse duration which allowed suitable hair samples of 25 mm$^2$ area exposures of 30 kW/mm$^2$ to 100 kW/mm$^2$, respectively. The basic output of this laser at 1.06 μm of 280 μJ energy with 4 ns pulse duration provided 100 kW/mm$^2$ exposure of the hair sample. In both cases, desired level of hair bleaching were obtained with a sequence of 10 laser pulses.

The lifetime of fluorescence of the melanin molecule has been found to be approximately 1.5 ns. Accordingly, it is believed that the reaction of chemical bond breakage of the melanin molecules should be as fast as its lifetime. Thus, the 30 μJ to 100 μJ energy of the laser at a wavelength of 530 nm as stated above, corresponds to 45 μJ/mm$^2$ to 150 μJ/mm$^2$ energy density delivered during the 1.5 ns lifetime of the melanin excited state. Likewise the corresponding energy of the laser light 1.06 μm wavelength corresponds to approximately 1.5 μJ delivered to a sample of 0.7 mm$^2$ during the 1.5 ns period. This provides energy and power densities of 150 μJ/mm$^2$ and 100 kW/mm$^2$.

It appears that these may be threshold conditions required in order to provide the necessary energy and power in order to destroy the melanin in order to achieve the photobleaching and lightening of the hair. Any other type of light source, whether laser or photoflash lamp would apparently require such threshold values, or the equivalence at particular wavelengths. By way of example, a short-high pressure Xenon lamp should be suitable for such application. These lamps are capable of delivering very concentrated light pulses energy of up to 0.5 J at a 10 μs pulse duration, thus giving the energy and power densities of 469 μJ/mm$^2$ and 312.5 kW/mm$^2$ respectively, related to the 1.5 ns pulse width.

Likewise some relatively inexpensive lasers, such as the Flashlamp Pumped Dye Laser would provide suitable use. Other types of light sources producing such radiation would also appear to be usable.

There has been described heretofore the best embodiments of the invention presently contemplated. However, it is to be understood that various changes and modifications may be made thereto without departing from the spirit of the invention.

What is claimed is:

1. A method of bleaching hair by exposing the hair to one or more effective bursts of radiation of artificial light whereby the radiation's intensity is sufficient to bleach melanin in the hair, wherein the light is generated from a laser or flashlamp source.

2. The method of claim 1, wherein the light is generated from a laser source operating at its basic frequency.

3. The method of claim 1, wherein the light is generated from a laser source operating at one of its harmonics.

4. The method of claim 1, wherein the light is generated from a flashlamp source.

5. The method of claim 1, wherein the light is generated from a solid state laser.

6. The method of claim 5, wherein the laser is based on one of a glass or crystalline lasing material.

7. The method of claim 6, wherein the laser is a neodymium glass laser.

8. The method of claim 6, where the laser is a ruby crystal lsser.

9. The method of claim 1, wherein the light is generated from a pumped laser or a flashlamp pumped dye laser.

10. The method of claim 1, wherein light is generated from an excimer pumped dye laser.

* * * * *